US00PP27981P3

(12) United States Plant Patent
Yurosek

(10) Patent No.: US PP27,981 P3
(45) Date of Patent: May 9, 2017

(54) POMEGRANATE TREE NAMED 'RED JAY'

(50) Latin Name: *Punica granatum*
Varietal Denomination: Red Jay

(71) Applicant: Y & Y MANAGEMENT COMPANY, LLC, Bakersfield, CA (US)

(72) Inventor: Jeffrey A. Yurosek, Bakersfield, CA (US)

(73) Assignee: Y&Y Management Company, LLC., Bakersfield, CA (US)

( * ) Notice: Subject to any disclaimer, the term of this patent is extended or adjusted under 35 U.S.C. 154(b) by 0 days.

(21) Appl. No.: 14/121,924

(22) Filed: Nov. 4, 2014

(65) Prior Publication Data

US 2016/0128255 P1 May 5, 2016

(51) Int. Cl.
*A01H 5/08* (2006.01)

(52) U.S. Cl.
USPC ..... Plt./210

(58) Field of Classification Search
USPC ..... Plt./210
See application file for complete search history.

(56) References Cited

U.S. PATENT DOCUMENTS

| | | |
|---|---|---|
| PP5,418 P | 3/1985 | Chater |
| PP5,685 P | 3/1986 | Kamada |
| PP16,578 P3 | 5/2006 | Smith |

*Primary Examiner* — June Hwu

(57) ABSTRACT

A new and distinct pomegranate variety named 'Red Jay', characterized by having a very early fruiting trait and dark red coloration in both internal seed arils and external skin. Fruit is sweet and juicy with a low acidity. Fruit is mature near Mid-August in the California Central Valley.

6 Drawing Sheets

Classification: The present invention relates to a new and distinct variety of pomegranate known botanically as *Punica granatum.*

Variety denomination: The new plant has the varietal denomination 'RED JAY'.

BACKGROUND OF THE NEW VARIETY

The present invention relates to a new and distinct variety of pomegranate tree referred to hereafter as the 'Red Jay' pomegranate tree, broadly characterized by its very early maturing habit, low acid content when ripe, and the deep red color of both the skin and seed arils.

The new variety of the present invention was discovered as a sport growing on a Wonderful (unpatented) pomegranate tree in a commercial planting in the inventor's farm near McFarland, Calif., USA. The instant variety was then asexually reproduced at the same farm in McFarland, Calif. by softwood cuttings made from the original sport with the resulting trees and fruit being identical to that original sport.

The fruit of the instant variety are mature for commercial harvest and shipment approximately August 5 or 25 days prior to the pomegranate variety 'Smith' (U.S. Plant Pat. No. 16,578) and 60 days prior to pomegranate variety 'Wonderful' (unpatented) in McFarland, Calif., USA. The new fruit is 10-15 days later maturing and has a distinctively darker skin and aril color when ripe than the 'Early Foothill' (unpatented). The new fruit is also 5-15 days later maturing with a darker red external and internal seed aril color than 'Granada' (U.S. Plant Pat. No. 2,618).

The State of California marketing regulations requires that pomegranate fruit may not be marketed until the juice from the arils have an acid content of no more than 1.85%. This new variety is able to meet this acid level requirement by July 25, however the fruit does not reach a marketable color until early August. While there are not any regulations related to required color, the market and consumers will generally not accept fruit and more specifically internal seed arils which are not red in color. By August 5, the instant variety is dark red externally with acceptably red internal seed arils. Generally, early fruit is desired by consumers and will attract higher prices for the grower, which makes this novel trait extremely desirable.

SUMMARY OF THE INVENTION

The new variety of pomegranate is generally characterized as having similar tree characteristics to the variety 'Wonderful' (unpatented), of which it is a sport, with exceptions that the instant variety matures 60 days earlier, has darker aril color when mature and has a shorter petiole length. Skin and seed aril color is darker red than varieties 'Smith' The new variety tree has medium to high vigor for pomegranate trees of similar age with an upright fountain shape and is slightly smaller than the variety 'Wonderful' (unpatented) when at the same maturity. Trunk surface is smooth similar to 'Wonderful' (unpatented) and more smooth than variety 'Smith' (U.S. Plant Pat. No. 16,578). Sugar content in early August will commonly test around 16-18 degrees brix, whereas 'Smith' (U.S. Plant Pat. No. 16,578) variety will have a brix level of 5-7 at the same time. Inflorescence period of 'Red Jay' starts in mid April and will usually reach 80% bloom by late April or early May.

TABLE I

| | RED JAY | WONDERFUL | SMITH |
|---|---|---|---|
| Bloom | Late April-Early May | Early-Mid May | Early May |
| Fruit Maturity | Early-Mid August | Early October | Early-Mid September |

TABLE I-continued

| | RED JAY | WONDERFUL | SMITH |
|---|---|---|---|
| Skin Color | Dark Red | Red | Bright Red/Pink |
| Aril/Seed Color | Very Dark Red | Red | Bright Red |
| Seed Hardness | Medium | Medium | Soft |

BRIEF DESCRIPTION OF PHOTOGRAPHS

Foliage in the photographs has been treated with a foliar protectant, which appears as speckles on the leaves. Foliage coloration is not speckled.

DETAILED BOTANICAL DESCRIPTION

Figure 1:
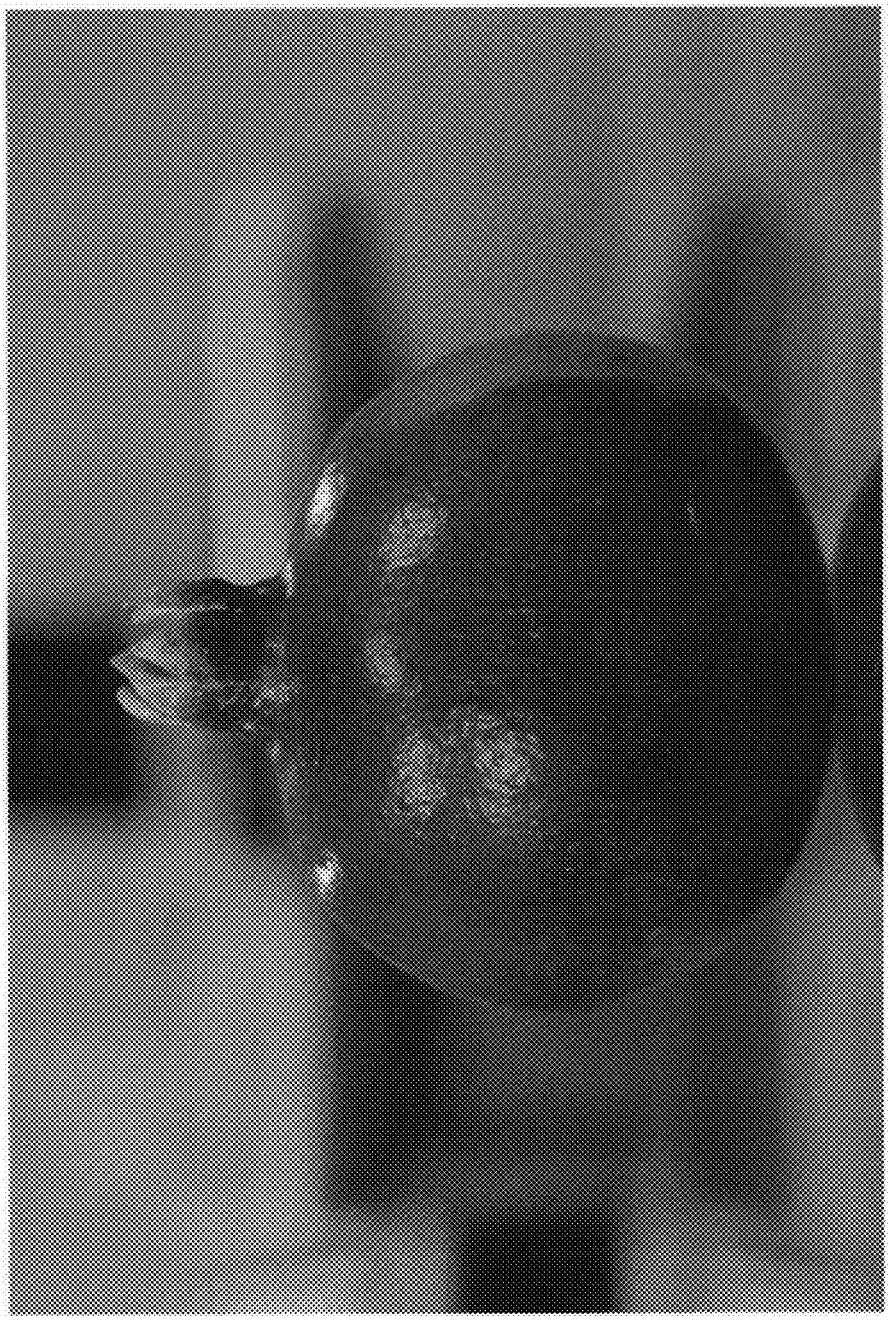
FIG. 1 is a side view of a typical fruit from 'Red Jay'.
Figure 2:
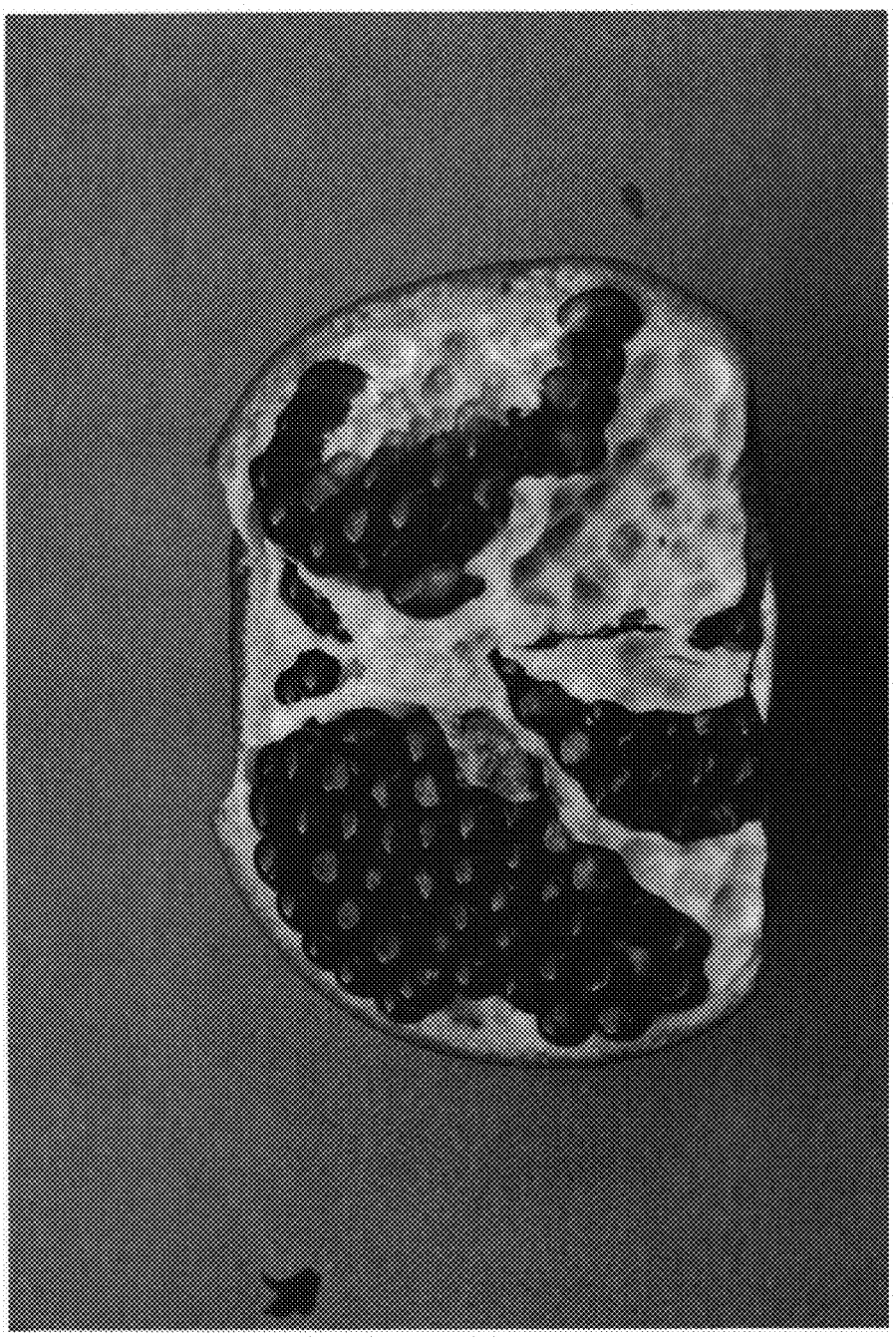
FIG. 2 is a section of a typical piece of fruit from 'Red Jay' with seed arils exposed.
Figure 3:
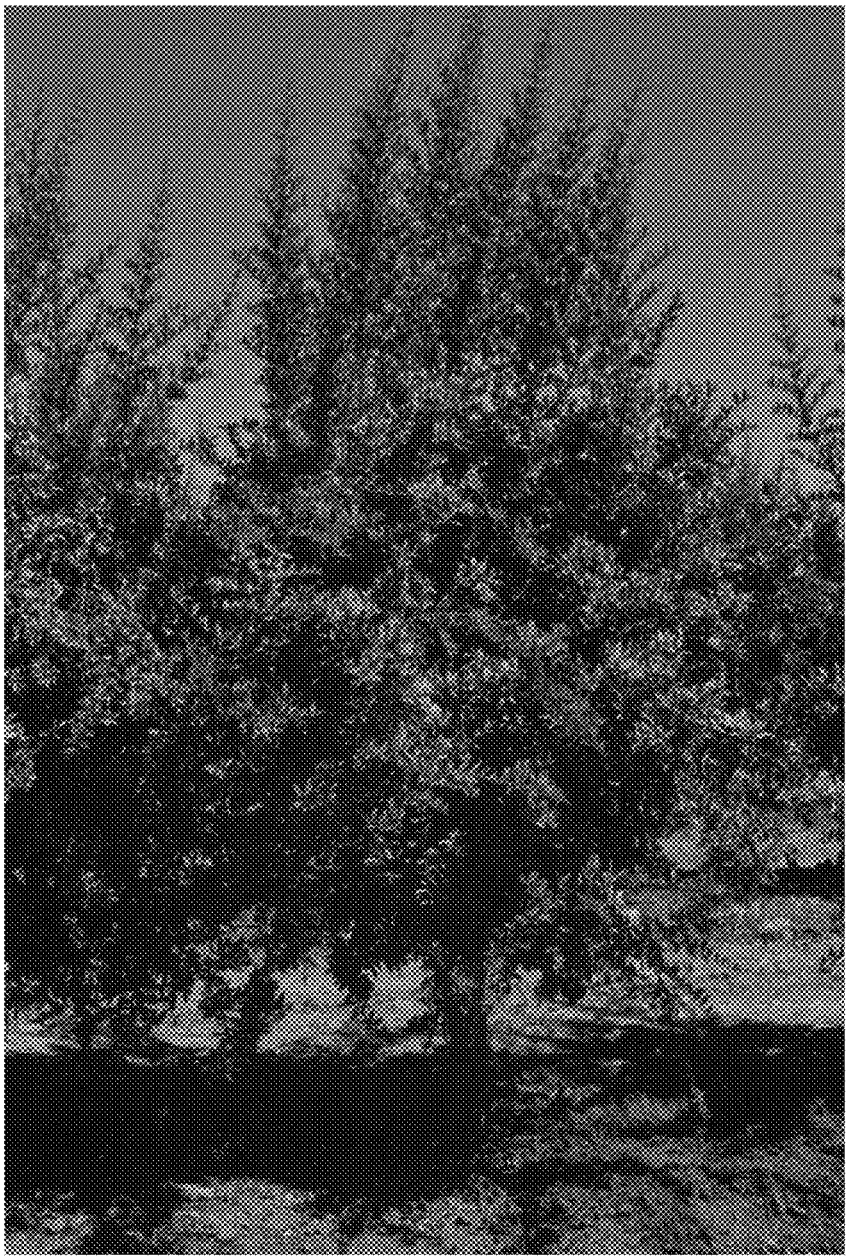
FIG. 3 is a view of a typical 3-year-old tree of 'Red Jay' tree.
Figure 4:
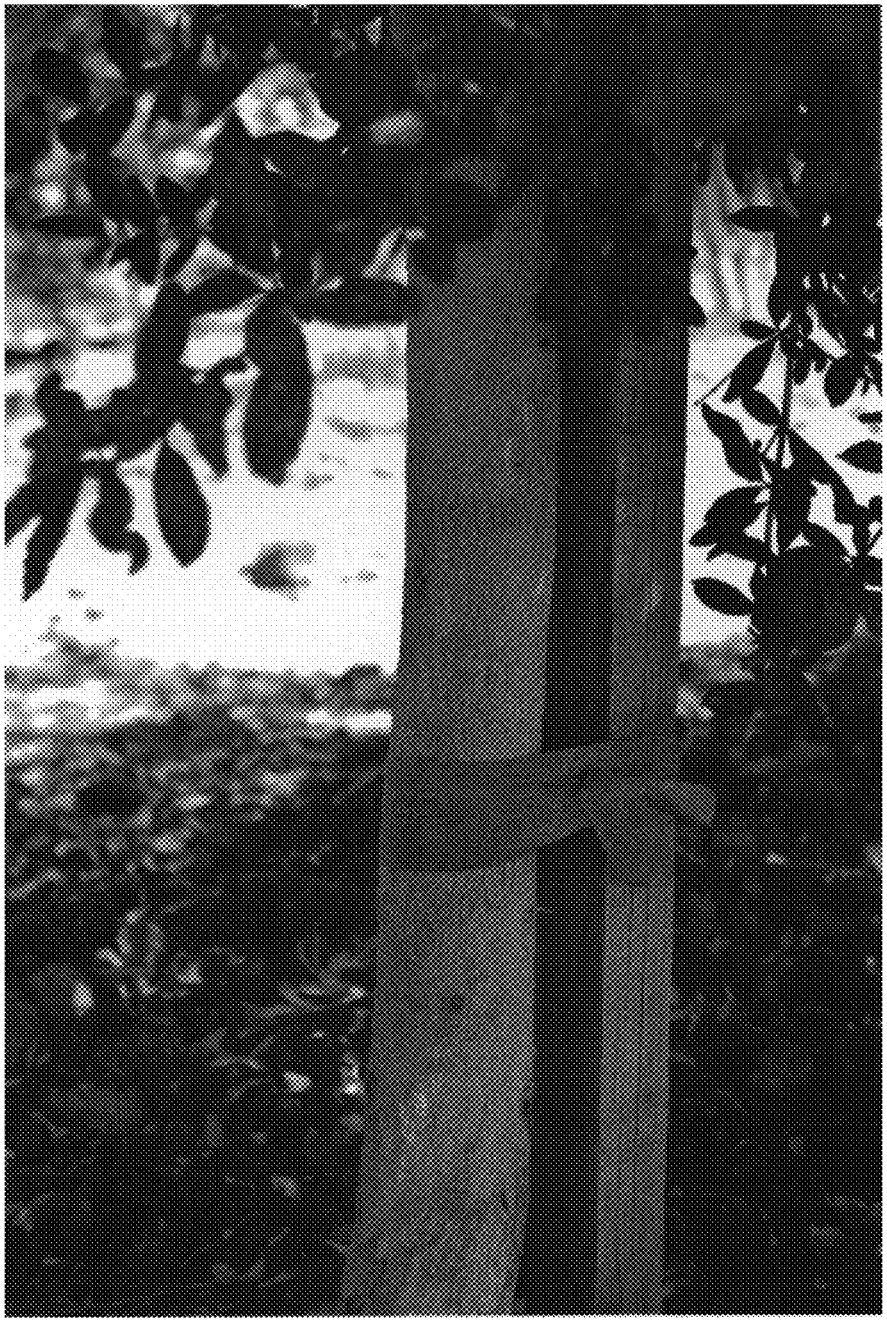
FIG. 4 is a close up view of a typical trunk of a three-year-old 'Red Jay'.
Figure 5:
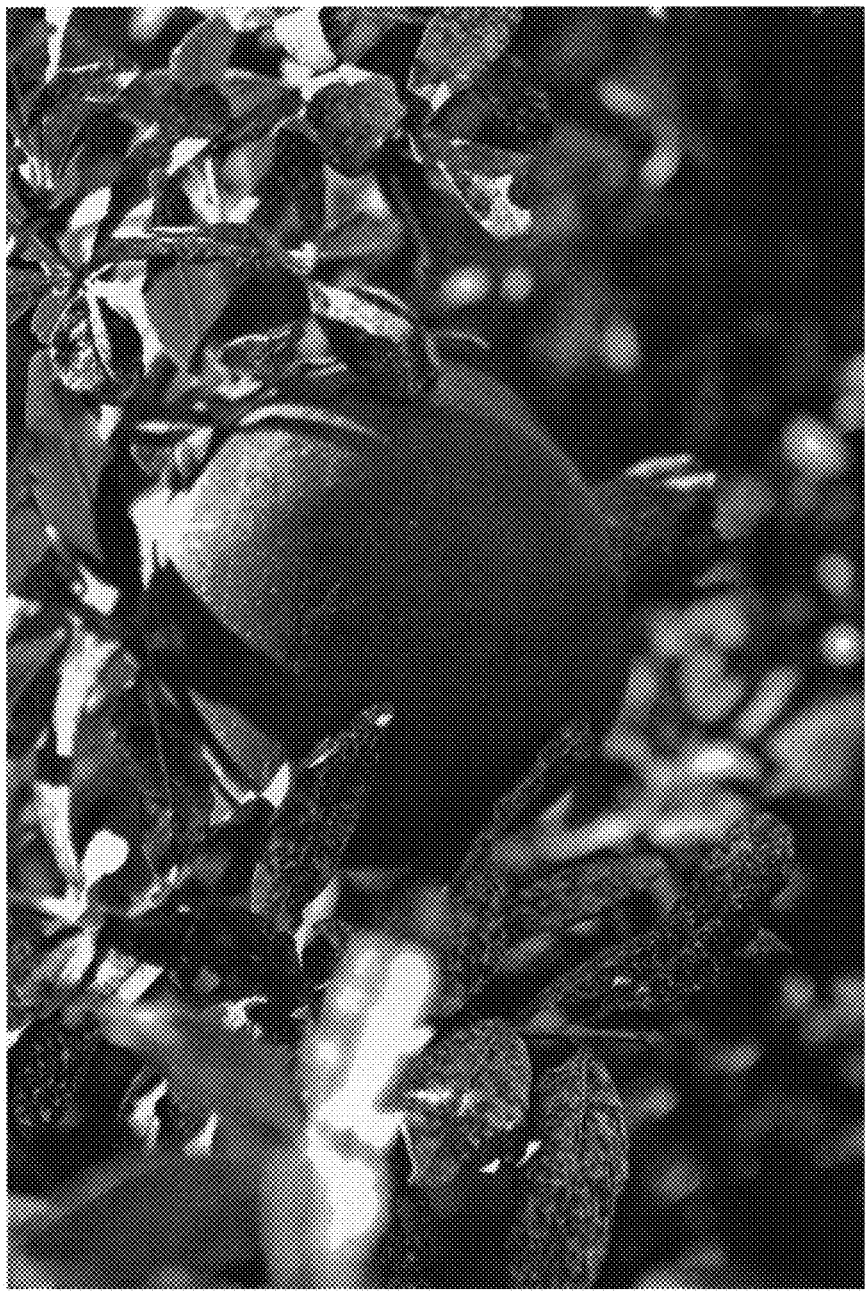
FIG. 5 is a close up view of fruit hanging in a 'Red Jay'.
Figure 6:
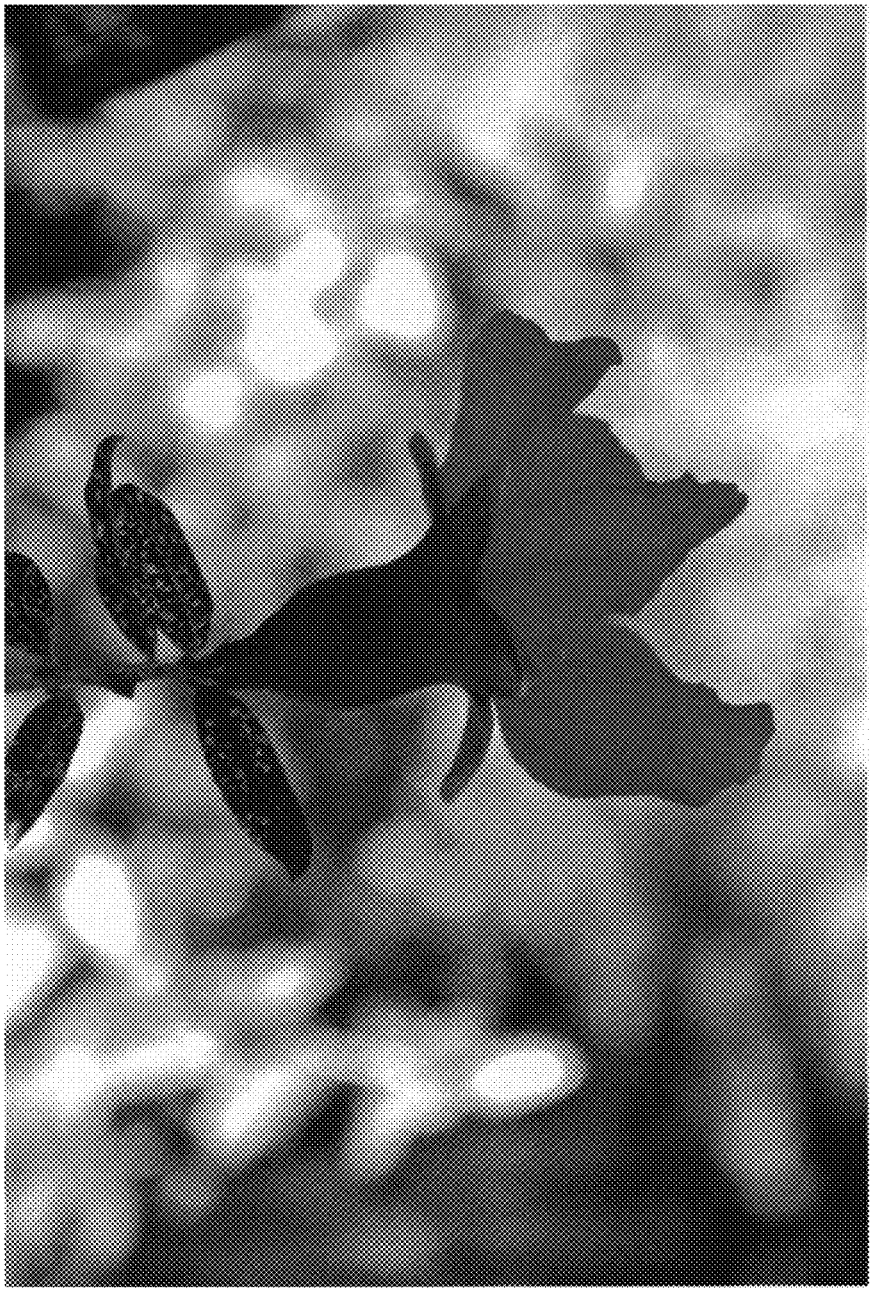
FIG. 6 is a close up side view of a typical flower of 'Red Jay'.

The following has been observed about the new variety 'Red Jay' during the last 3 years in the area of McFarland in Kern County in the Southern San Joaquin Valley of Calif. Phenotypical expressions may vary depending on changing environmental and climatic factors such as temperature, rainfall, and day length or by introduced external factors such as pruning, training, fertilization, and irrigation. All observations are from 3 year old trees unless otherwise stated. Color designations from Royal Horticultural Society Colour Chart, fifth edition.

Tree: Deciduous and not alternate baring.

*Size*.—Normal for pomegranate 10-12 feet in height and 7 to 8 feet in width, when pruned to commercial size.

*Vigor*.—medium to high — slightly less vigorous than 'Wonderful'.

*Figure*.—Upright fountain shape similar to 'Wonderful'.

*Trunks*.—Smooth surface appearance with 1 main trunk that easily produces suckers similar to 'Wonderful' but more smooth than pomegranate variety 'Smith'.

*Trunk diameter at* 30 cm.—60-65 mm similar to 'Wonderful'.

*Color*.—RHS 199D.

*Branch diameter* (*where bloom begins*).—6.00-6.35 mm.

*Branches*.—Slightly thorny.

*Color*.—RHS 199B.

*New growth*.—Near Yellow-Green N144A, lightly flushed Greyed-Purple 183D.

Foliage:

*Leaf growth habit*.—Symmetrically opposing, simple leaf.

*Petiole*.—1 mm to 4 mm in length — similar to 'Wonderful' but longer than varieties 'Granada' and 'Smith'. Background color near RHS 150A, streaked Greyed-Red 182A.

*Leaf shape*.—Slightly downward cupping with prominent midrib.

*Texture*.—Smooth glossy upper, matte under.

*Leaf color*.—RHS 143 A Upper, RHS 143B Under Leaves have been treated with a foliar protectant.

*Thorn description*.—Approximately 3 cm long, colored near 199B.

*Leaf length*.—38-40 mm.

*Leaf width*.—9.5-10 mm.

*Leaf margin*.—Entire.

*Leaf apex*.—Obtuse to slightly retuse.

*Leaf base*.—Rounded attenuate.

*Venation*.—Type: Pinnate Color: RHS 142 B.

*Stipule*.—Background color RHS 150 B, flushed 182A. Wing-like occurring length of petiole, approximately 1 to 4 mm long and 1 to 3 mm wide. Glabrous texture.

*Glands*.—None.

Flowers:

*Full bloom length*.—52 mm (beginning of sepal to flower tip).

*Open bloom width*.—47 mm.

*Blooming period*.—Early-Mid April or 10-15 days before 'Smith' variety and 20+ days before 'Wonderful' Variety.

*Bloom habit*.—2-5 per cluster, some singular, tubular bloom, open at abaxial end.

*Calyx depth*.—30-35 mm.

*Calyx width*.—38-40 mm.

*Calyx base color*.—RHS 53 A.

*Sepal length*.—13.5 mm on average.

*Sepal color*.—RHS 48 B.

5-7 *Sepals*.—On average. Apex acute, aspect slightly convex.

*Petal length*.—13-14 mm.

*Petal width*.—19-20 mm.

*Petal quantity*.—Average range 5 to 8.

*Petal apex*.—Obtuse.

*Petal texture*.—Moderately wrinkled all surfaces.

*Petal margin*.—Entire.

*Petal shape*.—Oval.

*Petal color*.—RHS 34A.

*Stamen length*.—6-8 mm.

*Stamen quantity*.—250-300 per flower.

*Filament color*.—Base near Red 53A, changing to 40A at apex.

*Anther color*.—Near Yellow 10B.

*Pistil*.—Singular pistil.

*Stigma length*.—5 to 6 mm Style Length: 10-13 mm.

*Style color*.—Near Greyed-Orange 169C, base near 153D.

*Stigma color*.—Near Yellow-Green 154A.

*Ovary length*.—16 mm.

*Ovary width*.—12-13 mm.

*Male and hermaphrodite flowers*.—Self and cross pollinating.

*Flower bud*.—Size: Average: 35 mm in height and 15 mm in length. Shape: Elongated sphere with upper section broader, balloon-like. Color: Near RHS Orange-Red 34A.

Fruit:

*Maturity*.—August 5 to 15 or 20-30 days prior to 'Smith' variety and 60+ days prior to 'Wonderful' variety. Fruiting is made up of several sets/flushes; there is also a late fruit set typical to most pomegranate varieties that either never matures or never reaches a marketable size.

*Average size.*—82.5 to 90 mm in diameter and slightly smaller than variety 'Wonderful'. Can grow up to 120 mm in diameter and 60-80 mm in length; size will continue to increase even after fruit has reached maturity.

*Height.*—60 to 80 mm.

*Aril width.*—4-5 mm.

*Aril length.*—8-9 mm.

*Shape.*—Normal for pomegranates, round shape with protruding calyx.

*Crown.*—Average height: when open 15-20 mm, closed 25-30 mm. Average diameter: when open 38-40 mm, closed 15 to 20 mm. Quantity of lobes: 5-8. Position of lobes: With maturity lobes flare outward.

*Average weight.*—450-500 g.

*Skin color.*—46-A RHS.

*Skin thickness.*—Medium.

*Septum color.*—Near RHS White 155D.

*Aril color.*—53-A RHS.

*Aril shape.*—Obovate: teardrop shape with flattened/faceted sides.

*Seed color.*—NN-155 B RHS.

*Seed size and shape.*—Irregular cylindric, with one end acute and one end truncate. Approximately 4 mm long and 1.5 mm wide.

*Fruit quality.*—Juiciness: High. Sweetness: High. cidity: Low.

Disease and pest resistance: Neither resistance nor susceptibility to normal diseases and pests of *Punica granatum* have been observed to date.

Temperature tolerance: To date, variety has been observed to thrive in USDA zone 9b. Further temperature range tolerance has not been observed to date.

Market: Fresh market for both whole fruit consumption and the processing of the aril seeds, and for juicing and supplement manufacturing.

I claim:

1. A new and distinct pomegranate tree variety as illustrated herein and described and characterized by having fruit which is substantially earlier maturing and darker red both in external and internal seed aril color.

* * * * *